(12) United States Patent
Assmann et al.

(10) Patent No.: US 11,700,592 B2
(45) Date of Patent: Jul. 11, 2023

(54) ADJUSTING A TRANSMISSION FREQUENCY OF A PHYSIOLOGICAL MONITORING UNIT

(71) Applicant: Siemens Healthcare GmbH, Erlangen (DE)

(72) Inventors: Bernd Assmann, Fuerth (DE); Juergen Roessler, Aurachtal (DE)

(73) Assignee: Siemens Healthcare GmbH, Erlangen (DE)

( * ) Notice: Subject to any disclaimer, the term of this patent is extended or adjusted under 35 U.S.C. 154(b) by 545 days.

(21) Appl. No.: 16/874,840

(22) Filed: May 15, 2020

(65) Prior Publication Data
US 2020/0359896 A1   Nov. 19, 2020

(30) Foreign Application Priority Data
May 15, 2019   (EP) .................................... 19174637

(51) Int. Cl.
| | |
|---|---|
| *H04W 72/02* | (2009.01) |
| *A61B 5/00* | (2006.01) |
| *A61B 5/282* | (2021.01) |
| *H04W 74/00* | (2009.01) |
| *A61B 5/026* | (2006.01) |
| *H04W 74/02* | (2009.01) |
| *G08B 1/08* | (2006.01) |
| *G08C 19/30* | (2006.01) |

(52) U.S. Cl.
CPC .......... *H04W 72/02* (2013.01); *A61B 5/0006* (2013.01); *A61B 5/0022* (2013.01); *A61B 5/0024* (2013.01); *A61B 5/026* (2013.01); *A61B 5/282* (2021.01); *A61B 5/6826* (2013.01); *A61B 5/7475* (2013.01); *G08B 1/08* (2013.01); *H04W 74/002* (2013.01); *H04W 74/02* (2013.01); *G08C 19/30* (2013.01)

(58) Field of Classification Search
CPC ...................................................... H04W 72/02
See application file for complete search history.

(56) References Cited

U.S. PATENT DOCUMENTS

| | | | |
|---|---|---|---|
| 8,437,843 B1 * | 5/2013 | Kayyali | A61B 5/6823 600/301 |
| 2009/0088605 A1 * | 4/2009 | Ross | G16H 40/67 370/312 |
| 2013/0245387 A1 * | 9/2013 | Patel | A61B 5/0002 600/300 |
| 2013/0289367 A1 | 10/2013 | Kruglick et al. | |
| 2015/0045699 A1 | 2/2015 | Mokaya et al. | |
| 2018/0192955 A1 * | 7/2018 | Al-Ali | A61B 5/02444 |

FOREIGN PATENT DOCUMENTS

DE   102008037388 A1   4/2009

OTHER PUBLICATIONS

European Search Report dated Oct. 18, 2019, for Application No. 19174637.9.

* cited by examiner

*Primary Examiner* — Travis R Hunnings
(74) *Attorney, Agent, or Firm* — Banner & Witcoff Ltd.

(57) ABSTRACT

Techniques are disclosed for adjusting a transmission frequency of a physiological monitoring unit, which includes a capture unit and a receiver unit. The capture unit and the receiver unit are wirelessly connected together and are configured to exchange data on the transmission frequency by means of a programming unit.

19 Claims, 4 Drawing Sheets

ADJUSTING A TRANSMISSION FREQUENCY OF A PHYSIOLOGICAL MONITORING UNIT

CROSS-REFERENCE TO RELATED APPLICATIONS

The present application claims the benefit of the filing date of European patent application no. EP19174637.9, filed on May 15, 2019, the contents of which are incorporated herein by reference in their entirety.

TECHNICAL FIELD

The present disclosure relates to techniques for adjusting a transmission frequency of a physiological monitoring unit and capturing a physiological signal.

BACKGROUND

In a magnetic resonance device, the body of an examination object that is to be examined (e.g. a patient) is usually subjected to a relatively high static magnetic field, e.g. 1.5 or 3 tesla, by means of a magnet. In addition, gradient pulses are output by means of a gradient coil unit. High-frequency (HF) pulses, e.g. RF excitation pulses, are then emitted by means of suitable antenna equipment via a high-frequency antenna unit, whereby the nuclear spins of specific atoms which are resonantly excited by these HF pulses are tipped by a defined flip angle relative to the magnetic field lines of the static magnetic field. The relaxation of the nuclear spins gives rise to the emission of HF signals, so-called magnetic resonance signals, which are received and then further processed by means of a receive unit comprising coil units that are configured as HF antennas. In this way, raw data is recorded that can ultimately be reconstructed for the desired image data.

During the recording of the raw data, any movement of the examination object typically has a negative influence on the raw data, and the image data to be reconstructed therefrom. But physiological movements, e.g. due to respiration and/or a beating heart, are difficult and/or impossible to avoid. If a physiological movement influences the examination region of the examination object, it is advantageous to adapt and/or synchronize the recording of the raw data with the physiological movement. For this purpose, physiological signals that are produced on the basis of the physiological movement are typically captured by means of a physiological monitoring unit.

Such a physiological monitoring unit typically comprises a capture unit and a receiver unit. In particular, the capture unit and at least one part of the receiver unit are typically arranged within an HF-screened space in which the magnetic resonance device is arranged. The capture unit may be arranged in the immediate environment of the examination object, preferably in direct contact therewith. The receiver unit may be configured to capture a physiological signal. The receiver unit may be configured to evaluate and/or process the physiological signal and/or is connected to a control unit for processing the physiological signal, wherein the control unit can also be configured to check and/or output gradient pulses and/or HF pulses.

Data, in particular data comprising physiological signals that are captured by the capture unit and/or data characterizing a form and/or a time-point of physiological signals to be captured by the capture unit, can be transmitted and/or exchanged wirelessly on a transmission frequency, the transmission frequency of the physiological monitoring unit, between the capture unit and the receiver unit. This transmission frequency may be fixed and/or preset. Depending on the location of the magnetic resonance device and/or the HF-screened space, the transmission frequency can be adversely affected by interfering signals and/or the transmission frequency may lie within a prohibited frequency band.

SUMMARY

The object underlying the disclosure is to specify an accurate method for adjusting a transmission frequency of a physiological monitoring unit. The object is achieved by the embodiments as described herein as well as the features described in the claims.

In an embodiment, the method for adjusting a transmission frequency of a physiological monitoring unit comprising a capture unit and a receiver unit, the capture unit and the receiver unit being wirelessly connected together and being configured to exchange data on the transmission frequency, comprises the following method steps:
   providing the transmission frequency by means of a programming unit,
   connecting the programming unit to the capture unit,
   transferring a first coding signal representative of the transmission frequency from the programming unit to the capture unit, and
   providing the transmission frequency to the receiver unit.
   The capture unit may be configured to capture a physiological signal of an examination object.

The programming unit may comprise a storage unit. When the transmission frequency is provided, the transmission frequency may be stored in the storage unit. The provision of the transmission frequency can be implemented by means of a user specification. The programming unit may also have a first interface, via which first interface the specification of the transmission frequency, e.g. by a user, can take place. The programming unit may be configured to receive and/or process an item of information comprising the transmission frequency, and/or to output the first coding signal and/or a second coding signal. The programming unit may comprise a second interface for connecting the programming unit to the capture unit and/or the receiver unit. The first interface and the second interface can be different from each other. The first interface and the second interface can both be integrated into the programming unit.

The receiver unit may be connected to a medical imaging device and/or a controller unit for the medical imaging device such as a magnetic resonance device, for example. The receiver unit may be configured to transfer the first coding signal and/or the transmission frequency to a controller unit for a medical imaging device. The coding signal representative of the transmission frequency may include the transmission frequency. The transmission frequency may be a predefined frequency. The transmission frequency may be defined in such a way that it lies outside the prohibited frequency band and/or differs from a frequency of a local interfering signal. A local interfering signal may be dependent on an individual location of the magnetic resonance device. The provision of the transmission frequency may involve a user specification and/or an automatic determination. The transfer of a first coding signal representative of the transmission frequency may include storing the transmission frequency on the capture unit. During use of the physiological monitoring unit, data may be exchanged between the capture unit and the receiver unit on a transmission frequency. The transmission frequency provided to the receiver unit corresponds to the transmission frequency comprised in the coding signal.

The method according to the disclosure makes it possible to change the transmission frequency of a physiological monitoring unit in a cost-effective manner. In particular, the transmission frequency of a conventional physiological monitoring unit can be changed in a software-based manner and/or without changing the hardware. In addition, it is not necessary to change the controller unit of the magnetic resonance device and/or to change control software that is to be executed thereon, since the change of the transmission frequency can be performed directly at the physiological monitoring unit. In addition, it is not necessary to provide a separate user interface and/or display on a controller unit and/or associated display unit which is configured to operate the magnetic resonance device. It is thereby possible to prevent incorrect operation by unauthorized and/or unqualified personnel.

The method according to the disclosure ensures that the capture unit and the receiver unit transmit, i.e. send and receive, data wirelessly on the transmission frequency, i.e. on the same frequency. Wireless transmission of data is therefore guaranteed at all times, in particular during operation of the physiological monitoring unit.

According to an embodiment variant of the method, the first coding signal comprises a trigger signal, and the transfer of the first coding signal comprises the signaling to the capture unit by the trigger signal of an intended change of the transmission frequency.

The capture unit may be configured to acknowledge the trigger signal when the first coding signal is transferred. The capture unit may be configured, upon acknowledging the trigger signal, to assume a status in which a change of the transmission frequency is permissible and a recording of physiological signals is preferably not permissible and/or is interrupted. The transmission of the trigger signal may initiate this status. It is possible, after the trigger signal for initiating this status has been acknowledged, for a user confirmation to be required before the transmission frequency is actually changed at the capture unit.

The trigger signal may be a defined signal sequence. In addition to the trigger signal, the first coding signal may include an additional signal representative of the transmission frequency. The trigger signal and the additional signal can be at least partially combined. The trigger signal and/or the first coding signal may be selected in such a way that it differs from a physiological signal which may be captured by the capture unit. A physiological signal may be, for example, a signal which is representative of an electrocardiogram and/or a human pulse. This embodiment variant allows an unambiguous identification of the start of the transfer of the first coding signal, representative of the transmission frequency, from the programming unit to the capture unit. It is thereby possible to embody the method in a particularly robust manner.

According to an embodiment variant of the method, the capture unit comprises a signal unit which indicates the connection of the programming unit to the capture unit. The signal unit can be configured as a light, for example, such as a light-emitting diode (LED) or other suitable light source. The signal unit can alternatively or additionally be audiologically configured.

The signal unit may signal the transfer of the first coding signal to the capture unit when the method is executed in accordance with this embodiment variant. The signal unit may signal the status in which a change of the transmission frequency is permissible and a recording of physiological signals is not permissible and/or is interrupted. The signal unit may indicate a first signal for this purpose. The signal unit may likewise be configured to indicate the operation of the physiological monitoring unit when physiological signals are being captured. For this purpose, the signal unit may indicate a second signal. The first signal may differ from the second signal. This embodiment variant allows feedback to a user executing the method that the transmission frequency is being changed and/or has been changed.

According to an embodiment variant of the method, the provision of the transmission frequency to the receiver unit is effected by means of an input by a user.

In this embodiment variant, the magnetic resonance device and/or a controller unit for the magnetic resonance device and/or for the physiological monitoring unit may include a user interface by means of which trained personnel and/or a user can transfer the transmission frequency to the receiver unit. This is a cost-effective solution for changing the transmission frequency which is transferred to the receiver unit and the capture unit in accordance with the present method embodiment.

According to an embodiment variant of the method, the receiver unit comprises an input and a receiver control unit, and the provision of the transmission frequency to the receiver unit comprises:
  connecting the programming unit to the input, and
  transferring a second coding signal representative of the transmission frequency from the programming unit to the receiver control unit.

The input preferably comprises an attachment point which allows a custom-fit attachment of the programming unit. The input can also be an interface, e.g. a wireless interface, e.g. for a Bluetooth connection. The receiver control unit is preferably configured to process data transmitted from the capture unit to the receiver unit and/or to transmit data to the capture unit and/or to prepare said data. This embodiment variant allows a software-based adjustment of the transmission frequency at the receiver unit and typically does not require any change to the hardware of the receiver unit. A cost-effective embodiment of the method is thereby possible, in particular since an upgrade of existing physiological monitoring units is not required. This embodiment variant can easily be executed by means of the programming unit, and also by an untrained user.

The second coding signal may comprise a trigger signal, and the transfer of the second coding signal may comprise the signaling to the receiver unit by the trigger signal of an intended change of the transmission frequency. The receiver unit may be configured to acknowledge the trigger signal when the second coding signal is transferred. The receiver unit may be configured, upon acknowledging the trigger signal, to assume a status in which a change of the transmission frequency is permissible and a recording of physiological signals is not permissible and/or is interrupted. The transmission of the trigger signal typically initiates this status. It is possible, after the trigger signal for initiating this status has been acknowledged, for a user confirmation to be required before the transmission frequency is actually changed at the receiver unit. The trigger signal may be a defined signal sequence. In addition to the trigger signal, the second coding signal may comprise an additional signal representative of the transmission frequency. The trigger signal and the additional signal can be at least partially combined. The trigger signal and/or the second coding signal may be selected in such a way that it differs from a physiological signal which may be captured by the capture unit. This embodiment variant allows an unambiguous identification of the start of the transfer of the second coding signal, representative of the transmission frequency, from the programming unit to the receiver unit. It is thereby possible to embody the method in a particularly robust manner.

According to an embodiment variant of the method, the capture unit comprises a sensor unit and a capture control unit, the sensor unit is configured to record physiological signals of an examination object, the programming unit comprises a coupling unit, and the connection of the programming unit to the capture unit includes an attachment of the coupling unit to the sensor unit. The sensor unit and the coupling unit may be configured in such a way that the attachment of the coupling unit to the sensor unit is effected in a custom-fit manner. This allows an intuitive and/or simple execution of the method according to this embodiment variant.

According to an embodiment variant of the method, the capture control unit is configured to distinguish the first coding signal from physiological signals. The first coding signal representative of the transmission frequency is preferably selected in such a way that it cannot be generated by a physiological attribute of a human. This may be, for example, a particularly intensive signal and/or a time characteristic which cannot be natural in origin. The coding signal is preferably selected in such a way that it differs from any possible human blood flow and/or human electrocardiogram. This embodiment variant allows an unambiguous identification of the transfer of the first coding signal representative of the transmission frequency from the programming unit to the capture unit. It is thereby possible to embody the method in a particularly robust manner.

According to an embodiment variant of the method, the sensor unit comprises at least two electrodes and is configured to capture an electrocardiogram; the coupling unit comprises at least one pin, and the attachment of the coupling unit to the sensor unit comprises a connection of the at least one pin to one of the at least two electrodes. The sensor unit is configured to capture an electrocardiogram by means of the at least two electrodes, e.g. by positioning the electrodes on an examination object (e.g. a patient). The at least one pin and/or the at least two electrodes are typically electrically conductive. Exactly one pin may be connected in each case to one of the at least two electrodes in an electrically conductive and/or custom-fit manner. The first coding signal may be transferred between the at least one pin and one of the at least two electrodes. The coupling unit can also comprise two or more pins.

The advantage of this embodiment variant is that, by virtue of the format of the programming unit, the latter can be attached to an existing interface of the capture unit, formed by the sensor unit in the form of electrodes for capturing an electrocardiogram. The programming unit is therefore easy to use and the method is particularly easy to execute.

According to an embodiment variant of the method, the transfer of the first coding signal comprises the output of a time-varying electric current. Therefore the first coding signal preferably has the same physical basis as the physiological signal. The first coding signal may differ in format from a physiological signal, e.g. in the temporal sequence and/or intensity of the electric current, so that it is possible to distinguish between the first coding signal and a physiological signal. This allows particularly efficient use of existing electrodes.

According to an embodiment variant of the method, the sensor unit is configured to capture a pulse of an examination object. The pulse is a physiological signal that is routinely monitored by means of a physiological monitoring unit. The method according to this embodiment variant can therefore be executed using a conventional physiological monitoring unit. This allows particularly efficient use of an existing sensor unit.

According to an embodiment variant of the method, the sensor unit comprises a finger clip, the coupling unit has the shape of a finger, and the connection of the programming unit to the capture unit comprises the coupling unit being surrounded by the finger clip.

According to this embodiment variant, the coupling unit has a shape which is such that it can be surrounded by the finger clip in a manner that is at least partially custom-fit. The first coding signal may be transferred between the finger clip and the coupling unit. The advantage of this embodiment variant is that, by virtue of the format of the programming unit, the latter can be attached to an existing interface of the capture unit, formed by the sensor unit in the form of a finger clip for capturing a pulse beat of the examination object. The programming unit is therefore easy to use and the method is easy to execute. The sensor unit, in particular the finger clip, may comprise an optical fiber. The coupling unit may comprise an optical fiber. Attachment of the coupling unit to the sensor unit may cause the respective optical fibers to be connected together, in particular the ends thereof. This allows particularly efficient use of an existing sensor unit and results in a robust method.

According to an embodiment variant of the method, the transfer of the first coding signal comprises the output of a time-varying light signal. The coupling unit in the shape of a finger can have a variable light permeability, which can be changed by the programming unit in accordance with the first coding signal, for example. Accordingly, the first coding signal can comprise a time-varying light signal. A trigger signal included in the first coding signal can also be a time-varying light signal. This embodiment variant allows cost-effective use of the existing sensor unit.

A method embodiment for capturing a physiological signal by means of a physiological monitoring unit comprising a capture unit and a receiver unit, the capture unit and the receiver unit being wirelessly connected together and being configured to exchange data on the transmission frequency, has the following method steps:

detecting the physiological signal by means of the capture unit, wirelessly transmitting the physiological signal from the capture unit to the receiver unit on the transmission frequency, and processing of the physiological signal by the receiver unit, wherein the transmission frequency of the physiological monitoring unit was previously adjusted in accordance with one of the embodiment variants set forth above.

Furthermore, the disclosure relates to a physiological monitoring system comprising a programming unit and a physiological monitoring unit comprising a capture unit and a receiver unit, which is configured to execute a method according to the disclosure for adjusting a transmission frequency.

Still further, the disclosure relates to a programming unit comprising a coupling unit and a programming control unit, which is configured to adjust a transmission frequency of a physiological monitoring unit comprising a capture unit and a receiver unit, these being wirelessly connected together and being configured to exchange data on the transmission frequency, wherein the programming control unit is configured to provide the transmission frequency and to generate a first coding signal representative of the transmission frequency, and the coupling unit is configured for connection to the capture unit and to transfer the first coding signal to the capture unit.

The advantages of the method for capturing a physiological signal, the physiological monitoring system, and the programming unit correspond essentially to the advantages of the method embodiments as described in detail above for adjusting a transmission frequency of a physiological monitoring unit. Features, advantages, or alternative embodiment variants cited in this context apply equally to the other claimed subject matter and/or embodiments, and vice versa.

BRIEF DESCRIPTION OF THE DRAWINGS/FIGURES

The above and other features and advantages of the present disclosure will be more apparent to those of ordinary skill in the art from the detailed description of preferred embodiments of the present disclosure with reference to the accompanying drawings, in which.

DETAILED DESCRIPTION

In order to make the object, technical solutions, and advantages of the present disclosure more apparent, the present disclosure will be further described in detail by way of embodiments hereinafter.

Figure 1:
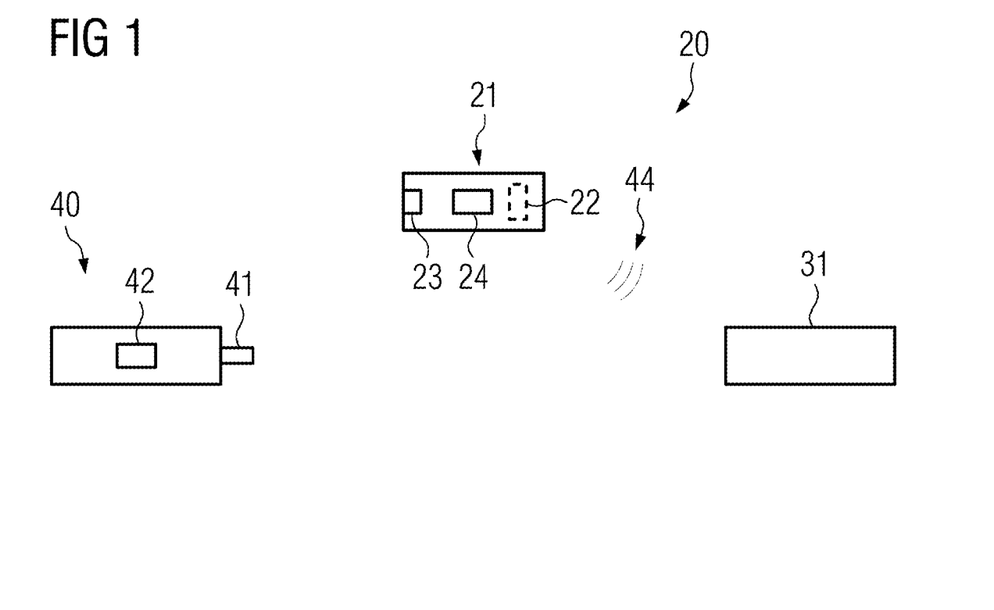
FIG. 1 shows a schematic illustration of an example physiological monitoring system, according to the disclosure in a first embodiment variant.

FIG. 1 shows a schematic illustration of an example physiological monitoring system, according to the disclosure in a first embodiment variant.

The physiological monitoring system comprises a programming unit 40 and a physiological monitoring unit 20 comprising a capture unit 21 and a receiver unit 31 (e.g. a receiver), which is configured to execute the method according to the disclosure for adjusting a transmission frequency 44 of the physiological monitoring unit 20. The capture unit 21 and the receiver unit 31 are wirelessly connected together and configured to exchange data on the transmission frequency 44.

The capture unit 21 may be alternately referred to as a physiological capture unit or a physiological data recording unit, and my comprise a signal unit 22 (e.g. notification circuitry), which indicates a connection of the programming unit 40 to the capture unit 21 and/or an acknowledgement of an intended change of the transmission frequency by means of the programming unit 40. The signal unit 22 can be configured such that the indication is visual or acoustic, for example. The signal unit can be configured in the form of a loudspeaker and/or an LED, for example. The signal unit 22 may signal further functions of the capture unit 21, e.g. when capturing a physiological signal of the examination object.

Figure 2:
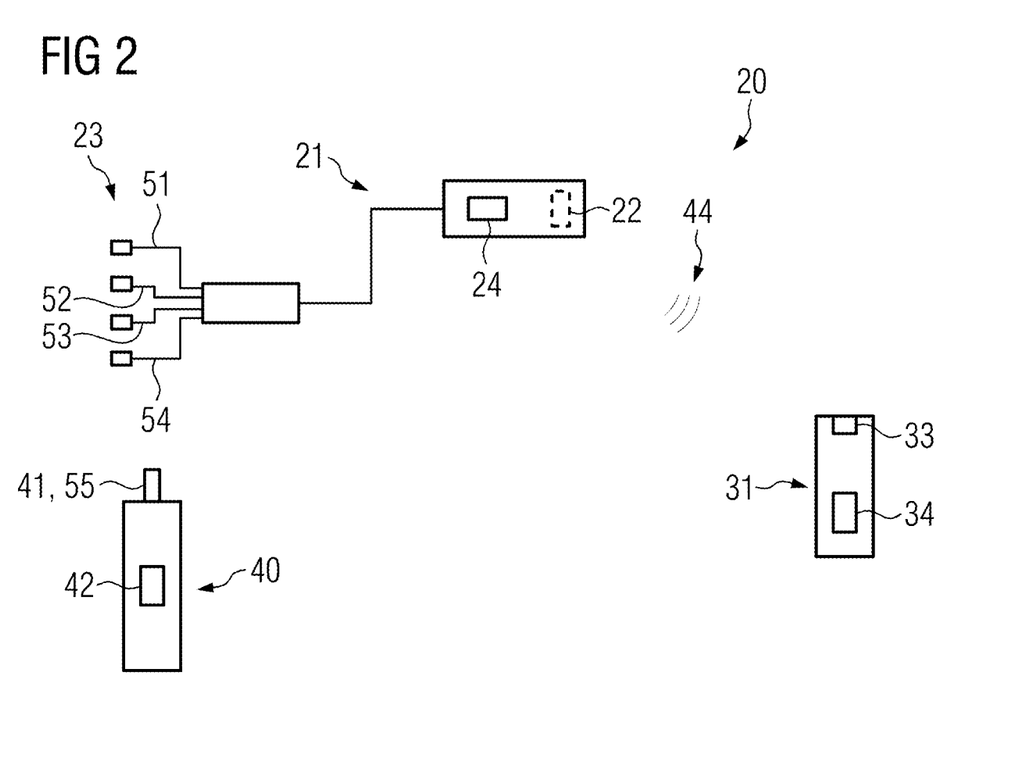
FIG. 2 shows a schematic illustration of an example physiological monitoring system, according to the disclosure in a second embodiment variant.

FIG. 2 shows a schematic illustration of an example physiological monitoring system, according to the disclosure in a second embodiment variant. The second embodiment variant is an optional extension of the first embodiment variant. The receiver unit 31 comprises an input 33 and a receiver control unit 34. The input 33 is embodied in such a way that the programming unit 40, e.g. a coupling unit 41 (e.g. a coupler or connector) forming part of the programming unit 40, can be connected to the input 33. The coupling unit 41 and the input 33 may be compatible with each other such that the coupling unit 41 and the input 33 can form a custom-fit and/or detachable connection and/or plug-type connection (e.g. mate with one another).

The capture unit 21 comprises a sensor unit 23, which is configured to record physiological signals of an examination object, and a capture control unit 24. The coupling unit 41 forming part of the programming unit 40 is configured to connect the programming unit 40 to the capture unit 21 by attaching the coupling unit 41 to the sensor unit 23. The sensor unit 23 comprises at least two (four in the embodiment variant illustrated) electrodes 51, 52, 53, 54, by means of which the sensor unit 23 is configured to capture an electrocardiogram. The coupling unit 41 comprises at least one pin 55. The at least one pin 55 is configured for attachment to one of the four electrodes 51, 52, 53, 54. The coupling unit 41 can comprise a plurality of pins, said pins being implemented such that one pin can be connected in each case to an electrode forming part of the sensor unit 23.

Figure 3:
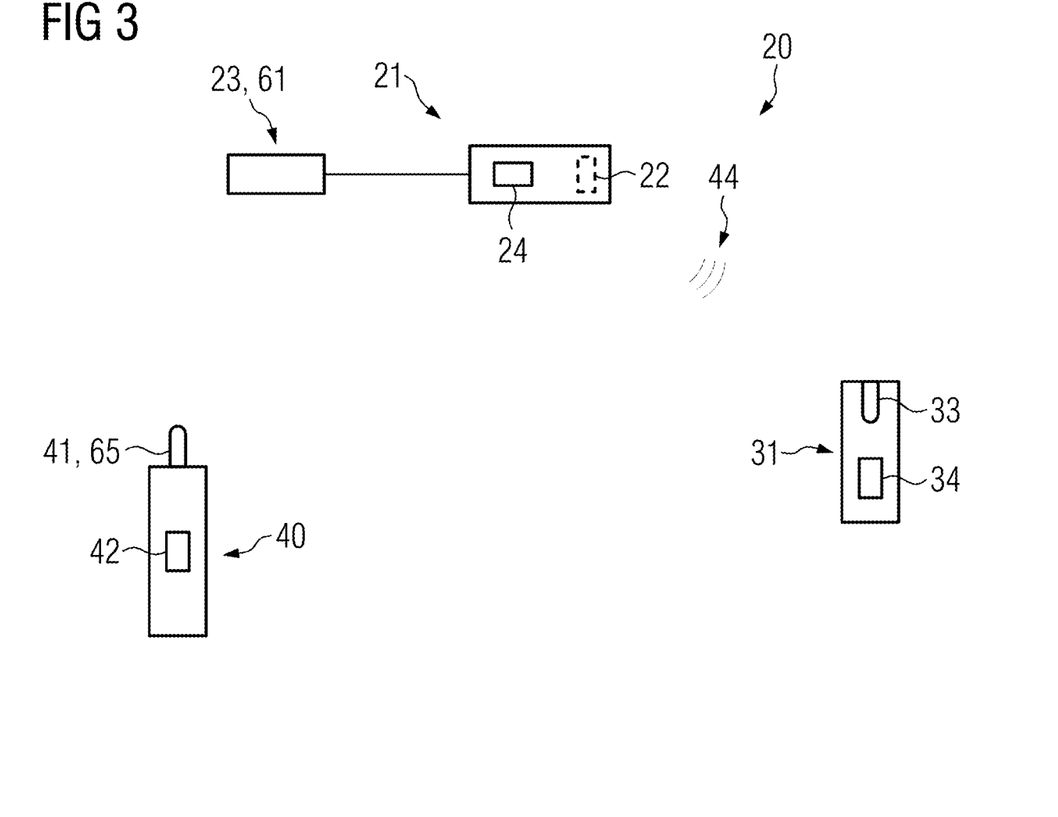
FIG. 3 shows a schematic illustration of an example physiological monitoring system, according to the disclosure in a third embodiment variant.

FIG. 3 shows a schematic illustration of a physiological monitoring system according to the disclosure in a third embodiment variant. The third embodiment variant is an optional extension of the first embodiment variant, and may be an alternative to the second embodiment variant.

The capture unit 21 comprises a sensor unit 23 and a capture control unit 24, said sensor unit 23 being configured to capture a pulse of an examination object. The sensor unit 23 in this case comprises a finger clip 61, which is configured to determine the pulse of the examination object with the aid of the finger thereof. The programming unit 40 comprises a coupling unit 41, 65 in the shape of a finger, and the connection of the programming unit 40 to the capture unit 21 comprises the attachment of the coupling unit 41 to the sensor unit 23 by means of the finger clip 61.

The receiver unit 31 comprises an input 33 and a receiver control unit 34. The input 33 is configured in such a way that the programming unit 40, in particular a coupling unit 41, 65 in the shape of a finger and forming part of the programming unit 40, can be connected to the input 33. The coupling unit 41 and the input 33 may be compatible with each other such that the coupling unit 41 and the input 33 can form a custom-fit and/or detachable connection and/or plug-type connection (e.g. mate with one another), and the input 33 is therefore so configured as to receive the coupling unit 41, 65 in the shape of a finger.

Figure 4:
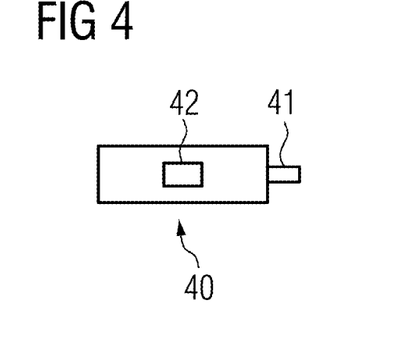
FIG. 4 shows a schematic illustration of an example programming unit, according to an embodiment of the disclosure.

FIG. 4 shows a schematic illustration of an example programming unit, according to an embodiment of the disclosure. The programming unit 40 comprises a coupling unit 41 and a programming control unit 42, which is configured to adjust a transmission frequency 44 of a physiological monitoring unit comprising a capture unit 21 and a receiver unit 31, these being wirelessly connected together and being configured to exchange data on the transmission frequency 44. The programming control unit 42 is configured to provide the transmission frequency 44 and to generate a first coding signal representative of the transmission frequency 44, and the coupling unit 41 is configured for connection to the capture unit 21 and to transfer the first coding signal to the capture unit 21. The coupling unit 41 can be configured, for example, in the shape of a finger 65 as per FIG. 3 or in the shape of a pin 55 as per FIG. 2. Moreover, the coupling unit 41 can be configured for connection to an input 33 of the receiver unit 31.

Figure 5:
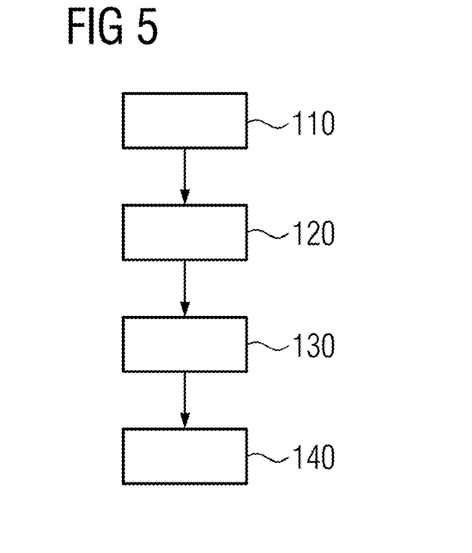
FIG. 5 shows an example sequence diagram of a first embodiment variant of a method according to the disclosure for adjusting a transmission frequency.

FIG. 5 shows a sequence diagram of a first embodiment variant of a method according to the disclosure for adjusting the transmission frequency 44. The method starts with method step 110, the provision of the transmission frequency 44 by the programming unit 40. In method step 120, the connection of the programming unit 40 to the capture unit 21 takes place, after which the transfer of a first coding signal representative of the transmission frequency 44 from the programming unit 40 to the capture unit 21 takes place in method step 130. In method step 140, the provision of the transmission frequency 44 to the receiver unit 31 takes place. Method step 140 can be effected by means of input by a user, for example.

Figure 6:
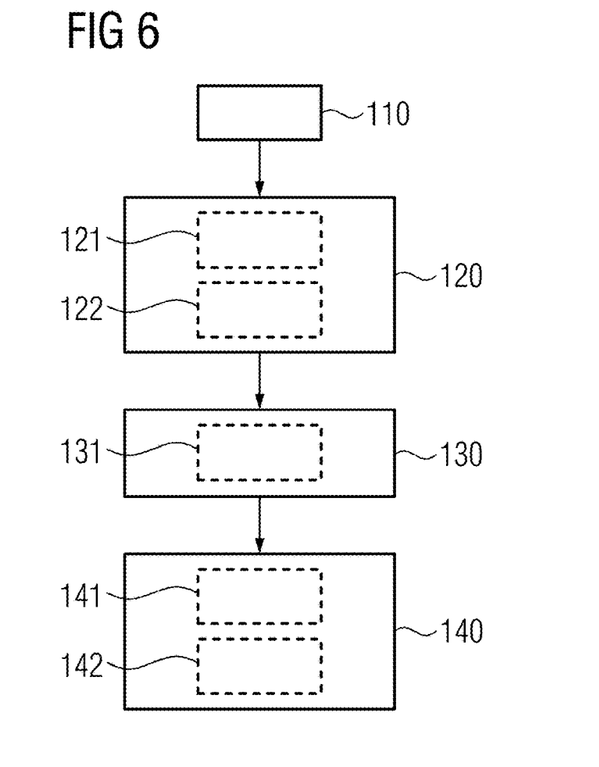
FIG. 6 shows an example sequence diagram of a second embodiment variant of a method according to the disclosure for adjusting a transmission frequency.

FIG. 6 shows a sequence diagram of a second embodiment variant of a method according to the disclosure for adjusting a transmission frequency 44. The second embodiment variant is an optional extension of the first embodiment variant.

If the capture unit 21 comprises a sensor unit 23 and a capture control unit 24, and the programming unit 40 comprises a coupling unit 41, method step 120 can include method step 121, an attachment of the coupling unit to the sensor unit.

If the sensor unit 23 includes at least two electrodes 51, 52, 53, 54 and is configured to capture an electrocardiogram, and the coupling unit 41 comprises at least one pin 55, method step 121 can include the attachment of the coupling unit 41 to the sensor unit 23, a connection of the at least one pin 55 to one of the at least two electrodes 51, 52, 53, 54. If the sensor unit 23 comprises a finger clip 61 and the coupling unit 41 has the shape of a finger 65, method step 120, in particular method step 121, can comprise the coupling unit 41 being surrounded by the finger clip.

The capture unit 21 can comprise a signal unit 22 which, in accordance with method step 122, outputs a signal and/or indicates an acknowledgement of the intended change of the transmission frequency in method step 120 and/or in method step 130.

If the first coding signal comprises a trigger signal, method step 130, the transfer of the first coding signal, can comprise method step 131, the signaling to the capture unit 21 by the trigger signal of an intended change of the transmission frequency 44. The capture control unit 24 may be configured to distinguish the first coding signal from physiological signals. Method step 130 can comprise e.g. the output of a time-varying electric current and/or light signal.

If the receiver unit 31 comprises an input 33 and a receiver control unit 34, method step 140, the provision of the transmission frequency 44 to the receiver unit 31, can include the following method steps:

method step 141, the connection of the programming unit 40 to the input 31, and method step 142, the transfer of a second coding signal representative of the transmission frequency 44 from the programming unit 40 to the receiver control unit 34.

Figure 7:
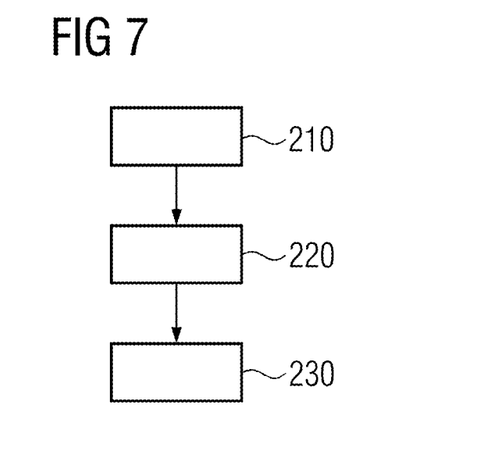
FIG. 7 shows an example sequence diagram of a method according to an embodiment of the disclosure for capturing a physiological signal.

FIG. 7 shows a sequence diagram of a method according to the disclosure for capturing a physiological signal by means of the physiological monitoring unit 20 comprising a capture unit 21 and a receiver unit 31, wherein the capture unit 21 and the receiver unit 31 are wirelessly connected together and are configured to exchange data on the transmission frequency 44. The transmission frequency 44 was previously adjusted in accordance with one of the method embodiments discussed herein. In method step 210, the detection of the physiological signal by means of the capture unit 21 takes place. In method step 220, the wireless transmission of the physiological signal from the capture unit 21 to the receiver unit 31 takes place on the transmission frequency 44. In method step 230, the processing of the physiological signal by the receiver unit 31 takes place.

Although the disclosure is illustrated and described in detail above by means of the preferred exemplary embodiments, the disclosure is not restricted by the examples disclosed, and other variations may be derived therefrom by a person skilled in the art without departing from the scope of the disclosure.

The various units as further discussed herein may be implemented as any suitable number and type of computer processors, and may perform their respective functions via hardware components, software components, or combinations thereof. Therefore, each of the devices as shown and described herein may alternatively be referred to as a "system," "circuitry," or a "device."

What is claimed is:

1. A method for adjusting a transmission frequency of a physiological monitoring device including physiological data recording circuitry and a receiver that are wirelessly connected to one another to exchange data on the transmission frequency, comprising:

providing, via a programming device, the transmission frequency;

connecting the programming device to the physiological data recording circuitry;

transferring, from the programming device, a first coding signal to the physiological data recording circuitry, the first coding signal being indicative of the transmission frequency; and providing, via the programming device, the transmission frequency to the receiver, wherein the physiological data recording circuitry comprises a sensor and capture control circuitry, wherein the sensor is configured to record physiological signals of an examination object, wherein the programming device comprises a connector, and wherein connecting the programming device to the physiological data recording circuitry comprises attaching the connector of the programming device to the sensor such that the connector of the programming device and the sensor are physically coupled to one another via a mated coupling arrangement.

2. The method as claimed in claim 1, wherein the first coding signal comprises a trigger signal, and wherein the transferring of the first coding signal comprises signaling, to the physiological data recording circuitry via the trigger signal, an intended change of the transmission frequency.

3. The method as claimed in claim 1,
wherein the physiological data recording circuitry comprises notification circuitry configured to indicate the connection of the programming device to the physiological data recording circuitry.

4. The method as claimed in claim 1, wherein the physiological data recording circuitry comprises notification circuitry configured to indicate the transfer of the first coding signal from the programming device to the physiological data recording circuitry.

5. The method as claimed in claim 1, wherein providing the transmission frequency to the receiver comprises providing the transmission frequency via user input.

6. The method as claimed in claim 1,
wherein the receiver comprises an input and receiver control circuitry, and
wherein providing of the transmission frequency to the receiver comprises:
connecting the programming device to the input; and
transferring a second coding signal indicative of the transmission frequency from the programming device to the receiver control circuitry.

7. The method as claimed in claim 1,
wherein the capture control circuitry is configured to distinguish the first coding signal from physiological signals to identify the first coding signal.

8. The method as claimed in claim 1, wherein:
the sensor comprises at least two electrodes and is configured to measure electrocardiogram data,
the connector comprises at least one pin, and
attaching the connector of the programming device to the sensor includes connecting the at least one pin to one of the at least two electrodes.

9. The method as claimed in claim 1,
wherein transferring the first coding signal from the programming device to the physiological data recording circuitry comprises outputting a time-varying electric current.

10. The method as claimed in claim 9,
wherein transferring the first coding signal from the programming device to the physiological data recording circuitry comprises outputting a time-varying varying light signal.

11. The method as claimed in claim 1,
wherein the sensor is configured to measure a pulse of an examination object.

12. The method as claimed in claim 1, wherein:
the sensor comprises a finger clip, and
the connection of the programming device to the physiological data recording circuitry comprises the connector of the programming device being surrounded by the finger clip.

13. Method as claimed in claim 1, wherein the mated coupling arrangement comprises a custom fit-fit attachment of the programming device to the physiological data recording circuitry.

14. The method as claimed in claim 1, wherein the sensor and the connector each comprises a respective optical fiber, and
wherein the mated coupling arrangement of the connector and the sensor couples ends of the respective optical fiber of the connector and the sensor to one another.

15. The method as claimed in claim 1, wherein the receiver is coupled to a magnetic resonance imaging device.

16. The method as claimed in claim 15, wherein the transmission frequency differs from a frequency of a local interfering signal, which is dependent on a location of the magnetic resonance device.

17. The method as claimed in claim 2, wherein the capture control circuitry is configured, after receiving the trigger signal, to change the transmission frequency upon receiving a user confirmation.

18. A method for capturing a physiological signal using a physiological monitoring device that includes physiological data recording circuitry and a receiver that are wirelessly connected to one another to exchange data on a transmission frequency, comprising:
transferring, via a programming device, a first coding signal to the physiological data recording circuitry, the first coding signal being indicative of a new transmission frequency that is different that a current transmission frequency used for exchanging data between the physiological data recording circuitry and the receiver;
providing, via the programming device, the new transmission frequency to the receiver;
adjusting, via the physiological data recording circuitry, the current transmission frequency to the new transmission frequency;
detecting, via the physiological data recording circuitry, the physiological signal;
wirelessly transmitting, from the physiological data recording circuitry, the physiological signal to the receiver on the new transmission frequency; and
processing, via the receiver, the physiological signal,
wherein the physiological data recording circuitry comprises a sensor and capture control circuitry,
wherein the programming device comprises a connector, and
wherein the programming device is connected to the physiological data recording circuitry by attaching the connector of the programming device to the sensor such that the connector of the programming device and the sensor are physically coupled to one another via a mated coupling arrangement.

19. A programming device, comprising:
a connector; and
programming control circuitry configured to adjust a transmission frequency used by a physiological monitoring device including physiological data recording circuitry and a receiver that are wirelessly connected to one another to exchange data on the transmission frequency,
wherein the programming control circuitry is configured to generate a first coding signal indicative of the transmission frequency, and
wherein the connector is configured to mate with the physiological data recording circuitry and to transfer the first coding signal to the physiological data recording circuitry,
wherein the physiological data recording circuitry comprises a sensor and capture control circuitry, and
wherein the programming device is configured to be connected to the physiological data recording circuitry by attaching the connector to the sensor such that the connector and the sensor are physically coupled to one another via a mated coupling arrangement.

\* \* \* \* \*